(12) United States Patent
Rodriguez

(10) Patent No.: US 11,596,585 B2
(45) Date of Patent: Mar. 7, 2023

(54) COMPOSITION FOR THE PREVENTION OF MICROBIAL GROWTH

(71) Applicant: Eikonic R&D Pty Ltd, Spring Hill (AU)

(72) Inventor: Ingrid Rodriguez, Spring Hill (AU)

(73) Assignee: Eikonic R&D Pty Ltd

( * ) Notice: Subject to any disclaimer, the term of this patent is extended or adjusted under 35 U.S.C. 154(b) by 0 days.

(21) Appl. No.: 15/738,652

(22) PCT Filed: Jun. 24, 2016

(86) PCT No.: PCT/AU2016/050543
§ 371 (c)(1),
(2) Date: Dec. 21, 2017

(87) PCT Pub. No.: WO2016/205892
PCT Pub. Date: Dec. 29, 2016

(65) Prior Publication Data
US 2018/0235852 A1 Aug. 23, 2018

(30) Foreign Application Priority Data

Jun. 26, 2015 (AU) .............................. 2015902486

(51) Int. Cl.
| | |
|---|---|
| *A61K 8/19* | (2006.01) |
| *A61Q 11/00* | (2006.01) |
| *A61P 31/04* | (2006.01) |
| *A61K 8/22* | (2006.01) |
| *A61K 33/40* | (2006.01) |
| *A61K 33/42* | (2006.01) |
| *A61K 33/00* | (2006.01) |
| *A61K 45/06* | (2006.01) |
| *A61K 33/22* | (2006.01) |
| *A61K 33/10* | (2006.01) |
| *A61K 33/20* | (2006.01) |
| *A61K 33/38* | (2006.01) |
| *A61K 33/06* | (2006.01) |
| *A61P 31/10* | (2006.01) |
| *A61P 31/02* | (2006.01) |
| *A61Q 17/00* | (2006.01) |
| *A61K 33/242* | (2019.01) |
| *A61K 8/24* | (2006.01) |
| *A61K 9/00* | (2006.01) |

(52) U.S. Cl.
CPC .................. *A61K 8/19* (2013.01); *A61K 8/22* (2013.01); *A61K 8/24* (2013.01); *A61K 33/00* (2013.01); *A61K 33/06* (2013.01); *A61K 33/10* (2013.01); *A61K 33/20* (2013.01); *A61K 33/22* (2013.01); *A61K 33/242* (2019.01); *A61K 33/38* (2013.01); *A61K 33/40* (2013.01); *A61K 33/42* (2013.01); *A61K 45/06* (2013.01); *A61P 31/02* (2018.01); *A61P 31/04* (2018.01); *A61P 31/10* (2018.01); *A61Q 11/00* (2013.01); *A61Q 17/005* (2013.01); *A61K 9/0014* (2013.01); *A61K 2800/413* (2013.01); *A61K 2800/74* (2013.01)

(58) Field of Classification Search
None
See application file for complete search history.

(56) References Cited

U.S. PATENT DOCUMENTS

| | | | |
|---|---|---|---|
| 5,437,858 A | 8/1995 | Hungerbach et al. | |
| 5,833,954 A * | 11/1998 | Chow | A23G 3/362 424/49 |
| 6,187,295 B1 * | 2/2001 | Glandorf | A61K 8/19 424/52 |
| 7,803,353 B2 * | 9/2010 | Lee | A61K 8/34 424/49 |
| 7,935,667 B2 | 5/2011 | Tichy et al. | |
| 2006/0263239 A1 * | 11/2006 | Tichy | A01N 59/16 422/28 |
| 2009/0269287 A1 * | 10/2009 | Berta | A61K 8/73 424/52 |
| 2010/0055138 A1 * | 3/2010 | Margulies | A61K 8/02 424/401 |
| 2015/0044299 A1 | 2/2015 | Esty | |
| 2015/0216765 A1 | 8/2015 | Le Ouay et al. | |
| 2016/0331670 A1 * | 11/2016 | Prencipe | A61K 8/25 |

FOREIGN PATENT DOCUMENTS

| | | |
|---|---|---|
| CN | 102090990 A | 6/2011 |
| EP | 0539651 A1 | 5/1993 |
| EP | 2905034 A1 | 8/2015 |
| WO | 2006093792 A1 | 9/2006 |

OTHER PUBLICATIONS

Sanli-Yurudu et al., "Efficacy of Collodial Silver-Hydrogen Peroxide and 2-Bromo-2nitroporopane-1,3-diol Compounds Against Different Serogroups of Legionella pneumophila Strains", Indian Journal of Microbiology (Jan.-Mar., 2012), vol. 52, No. 1, pp. 54-59.

(Continued)

*Primary Examiner* — Celeste A Roney
(74) *Attorney, Agent, or Firm* — Lerner, David, Littenberg, mholz & Mentlik, LLP

(57) ABSTRACT

A composition for reducing microbial activity in an environment susceptible to microbial activity, comprising: metallic nanoparticles; and an oxygenation agent.

13 Claims, 3 Drawing Sheets

(56) References Cited

OTHER PUBLICATIONS

Hernandez-Sierra et al., "The antimicrobial sensitivity of *Streptococcus* mutans to nanoparticles of silver, zinc oxide, and gold", Nanomedicine: Nanotechnology, Biology, and Medicine (Sep., 2008), vol. 4, pp. 237-240.
"MesoGold®—True Collodial Gold", Available from the Internet <URL: http://web.archive.org/web/20111222035453/http://koloidnestriebro.sk/index.php?language=en&page=mesogold>, Published Dec. 22, 2011 according to Wayback Machine, Last retrieved from the Internet Aug. 1, 2016.
International Search Report for PCT/AU2016/050543 mailed Aug. 8, 2016.
Supplementary European Search Report for EP Application No. 16813400, dated Feb. 7, 2019.

* cited by examiner (A)

(B)

(A)

(B)

(A)

(B)

COMPOSITION FOR THE PREVENTION OF MICROBIAL GROWTH

CROSS-REFERENCE TO RELATED APPLICATIONS

The present application is a national phase entry under 35 U.S.C. § 371 of International Application No. PCT/AU2016/050543 filed Jun. 24, 2016, which claims priority from Australian Patent Application No. 2015902486, filed Jun. 26, 2015, all of which are incorporated herein by reference.

TECHNICAL FIELD

The present invention relates to a composition for preventing the growth of disease related microbes. In particular, the invention relates to a composition comprising metallic nanoparticles and an oxygenation agent. The composition is useful in the treatment for reducing microbial activity in a number of environments susceptible to microbial activity, including the prevention of a disease or condition of the oral cavity. In particular, the composition is useful in the treatment or prevention of periodontal disease and/or tooth decay.

BACKGROUND OF INVENTION

Periodontal disease relates to a group of diseases that affect the tissues that support and anchor the teeth. Periodontal disease (also known as gum disease) exhibits inflammatory response and if left untreated, can result in bleeding and destruction of the gingival attachment and alveolar bone loss.

Periodontal disease affects human populations worldwide at high prevalence rates. Research suggests there are strong associations between chronic oral infections, particularly periodontitis and gingivitis, with a greater risk of diabetes, heart and lung disease, stroke, osteoporosis, low birth weight and premature birth. Currently, the treatment of periodontal disease is dominated by dental procedures such as scaling, root planning, and surgery. These procedures are generally invasive techniques and can be very costly to patients.

It would be desirable to provide a composition that addresses or at least ameliorates one or more disadvantages associated with current treatments.

Microbial activity is also invasive in many other environments, including infections in open wounds, contamination of water bodies, or infection of plant material.

It would be desirable to provide a composition that is able to reduce the microbial activity in such environments, whether that be by coating the body to prevent microbes penetrating, repelling the microbes, trapping and killing the microbes.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components, or group thereof.

SUMMARY OF INVENTION

The present invention relates to a composition for reducing microbial activity in an environment susceptible to microbial activity. The composition possesses the ability to either coat the body to which it is applied, repel the microbes, or trap and/or kill the microbes that come into contact with the composition. In one embodiment it may be used for the treatment or prevention of diseases or conditions of the oral cavity. In particular, the composition may be used for the treatment or prevention of periodontal disease.

In one aspect, the present invention provides a composition for reducing microbial activity in an environment susceptible to microbial activity comprising:
  metallic nanoparticles; and
  an oxygenation agent.

In some embodiments, the metallic nanoparticles comprise gold nanoparticles, silver nanoparticles, or combinations thereof. In particular embodiments, the metallic nanoparticles comprise gold nanoparticles.

In embodiments of the invention, the metallic nanoparticles have at least one dimension in the nanometre range. In some embodiments, the metallic nanoparticles have a diameter in the range of from about 2 to 200 nanometres. In embodiments, the metallic nanoparticles have a diameter in the range of from about 5 to 50 nanometres. In other embodiments, the nanoparticles have a diameter in the range of 18 to 22 nanoparticles.

The oxygenation agent employed in the composition may be selected from the group consisting of a peroxide, a perborate, a bicarbonate, a dioxide, and mixtures thereof. In some specific embodiments, the oxygenation agent is selected from the group consisting of hydrogen peroxide, sodium perborate, sodium bicarbonate, chlorine dioxide, and mixtures thereof. In a specific embodiment, the oxygenation agent is hydrogen peroxide.

In embodiments of the oral composition of the invention, the oxygenation agent is present in an amount of from about 1 to 35% of the composition. In some embodiments, the oxygenation agent is present in an amount of about 2% to 10% of the composition. In other embodiments, the oxygenation agent is present in an amount of about 5% of the composition.

The composition of the invention may further comprise a mineralization agent. When present, the mineralization agent is selected from the group consisting of calcium phosphate, dicalcium phosphate, tricalcium phosphate and calcium bicarbonate. In one form of the composition of the invention, the mineralization agent is tricalcium phosphate.

The mineralization agent may be present in composition in an amount of from about 2 to 20% (w/w) of the composition. In some embodiments, the mineralization agent is present in an amount of from about 5 to 16% (w/w) of the composition. In some embodiments, the mineralization agent is present in an amount of from about 10 to 14% (w/w) of the composition.

In some embodiments the composition, or variants of this composition without departing from the inventive concept, is contained in or contained on personal care products, cosmetics, wound treatment devices and bandages, water treatment compositions, oral formulations including mouth rinses, mouth swabs, toothpaste, orally dissolving strips, tooth powder, aerosol formulations, an inhalant, confectioneries, carbonated and non-carbonated drinks, chewing gums or compositions for the treatment of plants.

The environment susceptible to microbial activity preferably includes the mouth and teeth area of a subject, external body areas of a subject, wounds on a subject, plants and water environments.

In another aspect, the present invention also provides a method of treating or preventing the growth of disease-related microbes in the cavity of a subject comprising the step of contacting the microbes with a composition of any one of the embodiments as described herein.

In another aspect, the present invention provides for a method for providing a barrier to microbial activity by applying or incorporating a composition according to any one of the embodiments described herein in the mouth or teeth area of a subject, the external body area of a subject, to bandages or strips for application to a wound of a subject, plant material or water environment.

In another aspect, the present invention also provides a method of treating or preventing periodontal disease in a subject comprising the step of contacting the gingiva of the subject with a composition of any one of the embodiments described herein.

In another aspect, the present invention also provides use of a composition of any of the embodiments described herein in the preparation of a medicament, dressing or barrier for the prevention of microbial disease.

In another aspect, the present invention also provides use of a composition of any one of the embodiments described herein in the preparation of a medicament for the treatment or prevention of periodontal disease. In embodiments of the invention, a method is provided to prevent the growth or penetration of decay causing bacteria in a tooth or teeth of a subject by applying a composition as described herein to a tooth or teeth of a subject.

In embodiments of the invention, the periodontal disease is selected from the group consisting of gingivitis and periodontitis, and tooth decay.

The present invention also relates to all products comprising a composition of any one of the embodiments described herein.

DETAILED DESCRIPTION

Figure 1:
FIG. 1 shows typical LSCM images of yeast on 1.5 A (control) (a) and 1.5 C (b).
Figure 1:
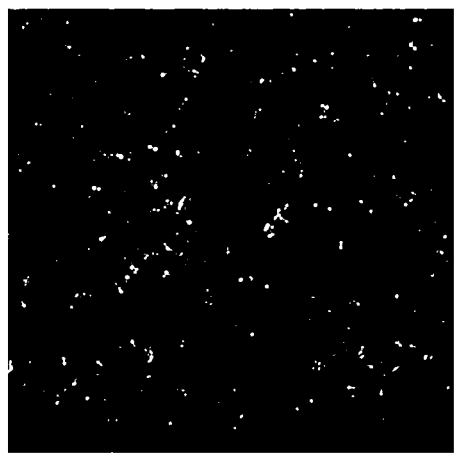

The present invention relates to a composition which is suitable for reducing microbial activity in an environment susceptible to microbial activity. Without being limited to theory, it is believed that the composition of the present invention is able to either provide a barrier to microbes by coating the body to which it is applied, repel the microbes, or trap within the composition the microbes, and/or kill the microbes with antimicrobial activity including decay causing bacteria. The composition may, in some embodiments, be suitable for the treatment or prevention of periodontal disease and dental caries. In such embodiments, the composition may be regarded as a periodontal composition.

The composition of the present invention may possess antimicrobial properties, and may be used on its own, or in adjunct with other oral hygiene treatments or vehicles, to treat or prevent diseases or conditions of the oral cavity such as periodontal disease.

In accordance with one aspect, the present invention provides a composition for reducing microbial activity in an environment susceptible to microbial activity comprising:
 metallic nanoparticles; and
 an oxygenation agent.

A number of metallic species have been shown to possess antimicrobial activity, including silver and gold. In particular, metals such as silver and gold are considered safe for in vivo use, and provide antimicrobial action without the possibility of developing antibiotic resistance.

In some embodiments of a composition of the present invention, the metallic nanoparticles comprise gold nanoparticles, silver nanoparticles, or combinations thereof. In one specific embodiment, the metallic nanoparticles comprise gold nanoparticles. Gold nanoparticles may be particularly suitable for the composition of the invention as it is non-toxic, biocompatible, inert and easily tolerated by the body.

The metallic nanoparticles may be in a suitable form. For example, when gold nanoparticles are used in the composition of the invention, the gold nanoparticles may be in a form selected from the group consisting of nanospheres, nanoplatelets and nanorods, or may be a combination of shapes including rods, cubes, discs and spheres.

Metallic nanoparticles used in the composition of the invention have at least one dimension in the nanometre range. In some embodiments, the metallic nanoparticles may suitably have a particle size in the range of from about 2 to 200 nanometres. In some embodiments, the nanoparticles have a particle size in the range of from about 5 to 50 nanometres. In some embodiments, the nanoparticles have a particular size in the range of from about 18 to 22 nanometres.

The composition may comprise an amount of metallic nanoparticles sufficient to achieve the required antimicrobial effects. In some embodiments, the composition may comprise from about 100 to about 1000 ppm of gold nanoparticles. In a specific embodiment, the oral composition may comprise about 300 to about 700 ppm, or from about 400 to about 600 ppm of gold nanoparticles.

The desired quantity of gold nanoparticles may be achieved by mixing a suitable amount of colloidal liquid gold with other agents used to prepare the composition. In some embodiments, the composition may comprise from about 1 to 20% (v/w), or from about 1 to 15% (v/w), or from about 3 to 10% (v/w) of colloidal liquid gold.

The composition of the present invention also comprises an oxygenation agent. It is desirable that the oxygenation agent possess antimicrobial properties. The combination of metallic nanoparticles with an oxygenation agent in the composition may enable the composition to exhibit an enhanced antimicrobial property.

In some embodiments, the oxygenation agent may be a source of reactive oxygen species. The reactive oxygen species may exert an antimicrobial effect against a range of pathogens, to kill the pathogens or inhibit their growth.

The composition of the invention comprises at least one oxygenation agent and may comprise a combination of two or more oxygenation agents. In some embodiments, the oxygenation agent may be selected from the group consisting of a peroxide, a perborate, a bicarbonate, a dioxide, and mixtures thereof.

In some specific embodiments, the oxygenation agent is selected from the group consisting of hydrogen peroxide, sodium perborate, sodium bicarbonate, chlorine dioxide, and mixtures thereof. In a specific embodiment, the oxygenation agent is hydrogen peroxide.

The oxygenation agent may be present in the composition in an amount that provides an antimicrobial effect. In some embodiments, the oxygenation agent is present in an amount of from about 1 to 35% of the composition. In some specific embodiments, the oxygenation agent is present in an amount of from about 2% to 20%, or from about 2% to 10%, of the composition. In one form, the oxygenation agent is present in an amount of about 5% of the composition.

One skilled in the art would understand that when the oxygenation agent is in the form of a solid (such for example, sodium perborate or sodium bicarbonate), then the reference to percentage amount (%) would be a reference to a weight/weight (w/w) or weight/volume (w/v) percentage, depending on the specific form of the composition. When the oxygenation agent is in the form of a liquid (such for example, hydrogen peroxide), then the reference to percentage amount (%) may be a reference to a volume/volume (v/v) or volume/weight (v/w) percentage, depending on the specific form of the composition.

The oxygenation agent may assist in the prevention of plaque build-up and gingivitis. In some embodiments, the oxygenation agent may also have a cosmetic effect in addition to controlling microbial growth in the oral cavity. For example, the oxygenation agent may also promote teeth whitening.

In some embodiments, the composition of the present invention may further comprise a mineralisation agent. The term "mineralisation agent" is used herein to refer to agents that promote the repair of alveolar bone following bone loss (re-mineralisation agents), as well as agents that reduce or prevent bone loss (de-mineralisation agents).

The mineralisation agent may be one that is conventionally used in dental therapy to provide calcium to inhibit or repair bone loss. In some embodiments, the mineralisation agent is selected from the group consisting of calcium phosphate, dicalcium phosphate, tricalcium phosphate and calcium bicarbonate.

Mineralisation agents such as calcium phosphate, dicalcium phosphate, tricalcium phosphate may be advantageous in the composition of the invention as such agents can provide calcium and phosphate ions and may help to restore, or inhibit the loss of, hydroxyapatite in affected bone and dental enamel.

When used in the composition of the invention, the mineralisation agent may be present in an amount of from about 2 to 20% (w/w) of the composition. In some embodiments, the mineralisation agent is present in an amount of from about 5% to 16% (w/w), or from about 10% to 14% (w/w), of the composition.

In a further aspect of the present invention, the composition is applied to an environment susceptible to microbial activity including the mouth and teeth area of a subject, external body areas of a subject, wounds in a subject, plants and water environments. The type of environments in which the composition may be used are not limited to oral healthcare but it may also be used in other external body areas, such as in deodorants and body sprays, and for the treatment of wounds, such as open wounds, whether applied directly, or by the application of a bandage or the like.

Other environments to which the composition may be applied include the application to plants to protect against microbial growth. This may be achieved by coating the plant to provide a barrier to the invasion of microbes. The composition may also repel or trap the microbes leading to killing the microbe.

The composition may also be useful in the prevention of microbial attack in the teeth by including it in carbonated or non-carbonated drinks that may include sugar, by providing a barrier to not only microbes, but also sugar.

In a further aspect, the present invention also provides a method of treating or preventing the growth of disease-related microbes in the oral cavity of a subject comprising the step of contacting the microbes with a composition as described herein. Thus the invention provides a means for killing or reducing microbes residing in the mouth, as well as inhibiting the growth thereof. The composition of the invention may be effective against a range of disease-related microorganisms in the oral cavity. In specific embodiments, the invention provides for a means for killing or preventing the growth of oral bacteria.

Disease-related microbes in the oral cavity may be gram-negative bacteria. Such bacteria include, but are not limited to, *Actinobacillus actinomycetemcomitans, Porphyromonas gingivalis, Bacteroides forsythus, Treponema denticola, T. socranskii, Prevotella intermedia, Fusobacterium nucleatum* and other oral bacteria.

In a further aspect, the present invention also provides a method of treating or preventing a disease or condition in the oral cavity of a subject comprising the step of administering a composition as described herein to the oral cavity of the subject. The disease or condition of the oral cavity may be periodontal disease.

Thus in some embodiments, the present invention provides a method of treating or preventing periodontal disease in a subject comprising the step of contacting the gingiva of the subject with a composition as described herein. In some embodiments, the periodontal disease is selected from the group consisting of gingivitis and periodontitis.

Periodontal disease is marked by bacterial overgrowth, which can lead to chronic inflammation of the gingiva and subsequent periodontal connective tissue destruction. The composition of the present invention is suitable for killing, or inhibiting the growth of, bacteria associated with periodontal disease. Thus, in some embodiments, the present invention provides a method for treating or preventing the growth of bacteria associated with periodontal disease. Such bacteria may be gram-negative bacteria. Bacteria implicated in periodontal disease and bone loss include, but are not limited to, *Actinobacillus actinomycetemcomitans, Porphyromonas gingivalis, Bacteroides forsythus, Treponema denticola, T. socranskii, Prevotella intermedia, Fusobacterium nucleatum* and other oral bacteria.

The Applicants have found that gram-negative bacteria and some yeasts adhere to the composition of the invention and the composition provides a barrier to such bacteria and yeasts infecting the environment. The composition does have antimicrobial activity and kills the adhered bacteria or yeast.

The Applicants have also found that the composition is able to repel gram-positive bacteria providing a barrier to such bacteria.

In another embodiment, the composition of the invention can be administered to the oral cavity of a subject in a form that is adapted to contact the gingiva of the subject. Suitable forms for the oral composition may include a paste, a gel, a mouthwash, a chewing gum, or powder. For example, in one embodiment the composition is administered in the form of a gel, powder or paste, which may be applied or rubbed onto a surface of the gingiva (free gingival margin and gingival sulcus), and optionally also onto a surface of one or more teeth, in order to treat or prevent periodontal disease. In some embodiments, the gel, powder or paste may be applied to the area of the oral cavity where the gingiva meets the teeth. In some embodiments, the gel, powder or paste may be applied to the region of the free gingival margin and gingival sulcus adjacent one or more teeth. In another embodiment, the composition may be administered to an oral cavity in the form of a chewing gum that is masticated by a subject. Mastication of the chewing gum enables the chewing gum to contact the gingiva of the subject. In another embodiment, the composition may be administered to an oral cavity in the form of a mouthwash, which is used to rinse the oral cavity and in this manner, can contact the gingiva of a subject.

It may be beneficial for the composition to be in a form that allows for contact with the gingiva of a subject for a time sufficient to allow the oral composition to provide a therapeutic effect. Exemplary contact times with the gingiva may be selected from the group consisting of at least 1 minute, at least 2 minutes, at least 5 minutes, or at least 10 minutes.

Bacteria associated with periodontal disease may reside in a periodontal pocket of a subject. Accordingly, in some embodiments, the oral composition of the invention is applied to a periodontal pocket of a subject to treat or prevent periodontal disease. In such embodiments, the metallic nanoparticles may be retained in the periodontal pocket and in this manner, be capable of exerting a sustained antimicrobial effect for the treatment or prevention of periodontal disease.

The composition of the invention may be topically applied to the gingiva of a subject. In this manner, the composition of the invention can provide a less invasive form of treatment of oral diseases and conditions such as periodontal disease. In some embodiments, the composition may be topically applied to the area of the oral cavity where the gingiva meets one or more teeth. In some embodiments, the composition may be topically applied to the region of the free gingival margin and gingival sulcus adjacent one or more teeth.

The composition may also comprise one or more agents, carriers or excipients conventionally used in the art. For example, the composition may comprise antiplaque or anti-calculus agents, fluoridating agents, colouring agents, plasticising agents, sweeteners, flavouring agents, solvents, binding agents, surfactants, emulsifiers, humectants, pH balancers, solubilisers, preservatives or thickeners. The composition may be formulated with carriers or excipients that may help to generate the desired form for administration to the oral cavity.

In another aspect, the present invention provides a method for providing a barrier to microbial activity by applying or incorporating a composition as described herein, in the mouth or teeth area of a subject, the external body area of a subject, to bandages or strips for application to a wound of a subject, plant material or water environment.

In another aspect, the present invention also provides use of a composition of any one of the embodiments described herein in the preparation of a medicament, dressing or barrier for the prevention of microbial disease. In another embodiment the invention provides use of a composition of any one of the embodiments described herein in the preparation of a medicament for the treatment or prevention of a disease or condition of the oral cavity. The disease or condition may be periodontal disease. In some embodiments, the periodontal disease is selected from the group consisting of gingivitis and periodontitis.

As used herein, the term "subject" generally refers to a mammalian subject. The subject may be a human or animal.

EXAMPLES

The following example illustrates the present invention in further detail however the example should by no means be construed as limiting the scope of the invention as described herein.

Example 1

An oral composition in the form of a paste is prepared as follows:

| Ingredient | Quantity |
| --- | --- |
| gold nanoparticles | 0.05% |
| 35% food grade hydrogen peroxide | 5% |
| tricalcium phosphate | 12% |
| polysorbate (surfactant) | 1% |
| arabic gum (binding agent) | 1% |
| sorbitol (humectant) | 35% |
| peppermint essential oil (flavouring agent) | 2% |
| xylitol (sweetener) | 2% |
| natural grapefruit seed (preservative) | 5-6% |
| Water | to 100% |

To prepare the oral paste, a liquid base is first prepared with water, sorbitol and arabic gum. The gold nanoparticles, hydrogen peroxide, xylitol and natural grapefruit seed are added to the liquid base and dispersed. Tricalcium phosphate is then added and blended with the mixture. The flavouring agent is then added and mixed. The polysorbate (surfactant) is added last under slow speed agitation to minimise foaming.

Example 2

This example outlines the initial formulation and investigation into the efficacy of a new dental treatment to combat dental caries, apical periodontitis and periodontal diseases. Advanced microscopy techniques were used to examine the interactions between model microbial species and formulations of the product. The model species *Fusobacterium nucleatum* a Gram negative, *Streptococcus mutans* a Gram positive, implicated in periodontal disease and dental decay; and *Saccharomyces cerevisiae* to represent yeasts, which are also found in dental plaque were investigated.

Material Preparation

Samples were made using three ingredients:
Peroxide solution: 5% hydrogen peroxide: 2-3 gms of 5% solution
Active liquid ingredient: Colloidal gold liquid (gold nanoparticles): 7-8 gm of liquid
Powder component: tricalcium phosphate—approx. 12 gms Firstly the peroxide solution was made by mixing a concentrated peroxide with water. The active liquid ingredient was then added. The final stage was to add the powder component and mix by hand using a spatula. All quantities were measured by mass rather than volume.

Mixing at the predetermined concentrations provided a runny liquid so it was decided to make further samples using 50% more powder component. This gave a thicker material with a toothpaste like consistency. Control samples were made with the active ingredient substituted for an equal mass of water. The samples produced were therefore as follows:

- 1×A—Sample with active ingredient at standard powder concentration
- 1×C—Sample without active ingredient at standard powder concentration
- 1.5×A—Sample with active ingredient at 1.5× powder concentration
- 1.5×C—Sample without active ingredient at 1.5× powder concentration Additional samples were also produced in the same way but subjected to heating after mixing. These samples were heated at 60° C. for 10 minutes in a water bath.

Initial microbial tests showed greater activity for the 1.5 active ingredient mixture, so antimicrobial tests concentrated on this formulation. The formulation without the active ingredient served as a control within the subsequent antimicrobial tests.

Application of Sample to Glass

The testing of the material with various media required the samples to be applied to glass slides or cover slips. The more liquid 1× samples were applied via a pipette and allowed to run down the glass. This was sufficient to evenly coat the glass. The thicker 1.5× samples were spread onto the glass using a pipette. The initial measurement for tricalcium phosphate was 8 gms, but a further 4 gms was added, and the 12 gms of tricalcium phosphate gave a better consistency.

During preparation of samples, it was observed that a drying time of approximately 5 minutes gave optimal adhesion of material to the glass. Fully dried samples lifted off the glass readily when immersed in the liquid media, while freshly prepared samples also tended to lift off but to a lesser extent. This problem was hard to avoid for this water based dispersion and gave unevenness in the coated glass following immersion.

Laser Scanning Confocal Microscopy (LSCM)

A light microscopy technique was used in conjunction with staining to identify whether bacteria were alive or dead on the formulations. The sample substrates were immersed in a suspension of microbes and incubated for 24 hours to encourage the growth of biofilm. This time period would allow the cells to adhere to the surface and the development of a biofilm, which involves the recruitment of cells from the bulk suspension, surface growth and the release of extracellular polysaccharides. These processes promote the attachment of the population to the surface and occur in the development of dental plaque.

S. cerevisiae (Model Yeast)

The study observed that when the active ingredient was included there was an increase in cell adhesion and cell kill as there appears to be a slightly higher proportion of cells stained red which are dead compared to the green stained cells which are alive.

FIG. 1 presents LSCM images of stained yeast cells. This work was repeated twice with the same outcome.

F. nucleatum (Gram Negative Model Organism)

A similar behaviour was observed for F. nucleatum with increasing numbers of cells attached to the composition when the active ingredient was present. There was also an increase in the number of dead cells indicating a bactericidal action for the active ingredient.

Figure 2:
FIG. 2 shows typical LSCM images of *F. nucleatum* on 1.5 A (control) (a) and 1.5 C (b).
Figure 2:
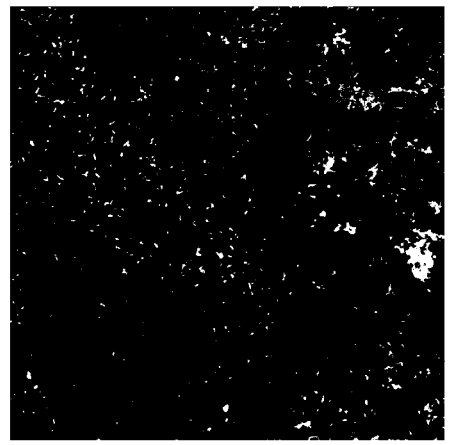

FIG. 2 presents LSCM images of stained F. nucleatum cells on the formulation.

S. mutans (Gram Positive Model Organism)

The cell surface of Gram Positive bacteria has a significantly different structure from that of Gram negative bacteria, so their chemical and physical interactions are often different. Thus, we weren't surprised when the study observed a different action for the active ingredient when S. mutans a Gram positive bacteria was exposed to the formulation. There were more cells observed on the control samples compared to the formulation with the active ingredient. We were unable to identify if there were increased numbers of dead cells after exposure to the active ingredient.

Figure 3:
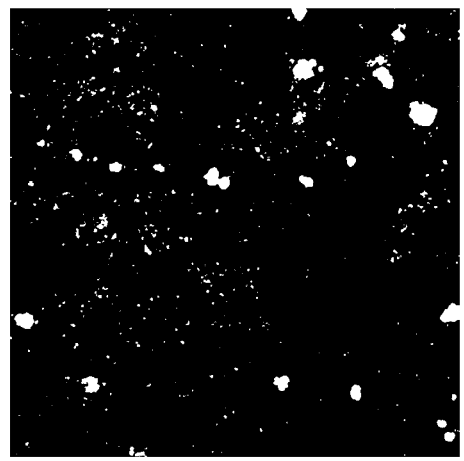
FIG. 3 shows typical LSCM images of *S. mutans* on 1.5 A (control) (a) and 1.5 C (b)
Figure 3:

FIG. 3 presents LSCM images of stained S. mutans cells on the formulation.

CONCLUSIONS

In conclusion, we have observed that there is antimicrobial activity for the initial formulation, which is different for Gram positive and Gram negative bacteria. For S. mutans a Gram positive bacterial species there was reduced adhesion and biofilm formation at the surface containing the active ingredient compared to that at the control surface. Reduction of cell adhesion is one method that can be used to reduce microbial colonisation of surfaces. The surfaces in the mouth are prime targets for control methods that lower adhesion, as these will attenuate natural methods that clean the mouth which include surface shear caused by chewing, the tongue and brushing. Such methods, that reduce microbial adhesion, may also render existing biofilms more susceptible to shear. For Gram negative F. nucleatum the active ingredient increased attachment and biofilm formation. Increase in adhesion was also observed for the yeast population at the treated formulation. In both cases the active ingredient showed some antimicrobial action with an increased proportion of dead cells at the treated surface. This is interesting with potential as an approach to combat plaque formation by the preferential adhesion to surfaces that have a bactericidal affect and/or are later removed from the teeth and gums leaving pristine teeth and tissues.

Future patent applications may be filed in Australia or overseas on the basis of, or claiming priority from, the present application. It is to be understood that the following provisional claims are provided by way of example only, and are not intended to limit the scope of what may be claimed in any such future application. Features may be added to or omitted from the provisional claims at a later date so as to further define or redefine the invention or inventions.

Finally, it is to be understood that various other modifications and/or alterations may be made without departing from the spirit of the present invention as outlined herein.

The invention claimed is:

1. A composition for reducing microbial activity in an environment susceptible to microbial activity, consisting of:
   - gold nanoparticles;
   - hydrogen peroxide;
   - a mineralization agent selected from the group consisting of calcium phosphate, dicalcium phosphate, and tricalcium phosphate; and
   - water,
   wherein the composition is an aqueous composition configured to be suitable for oral use.

2. A composition according to claim 1 wherein the gold nanoparticles have a diameter in the range of from about 2 to 200 nanometers.

3. A composition according to claim 1 wherein the hydrogen peroxide is present in an amount of up to about 35% of the composition.

4. A composition according to claim 1 wherein a concentration of the gold nanoparticles in the composition is from about 100 to about 1000 ppm.

5. A composition according to claim 1 wherein the mineralization agent is tricalcium phosphate and is present in an amount of from about 2 to 20% (w/w) of the composition.

6. A method of treating or reducing the growth of disease-related microbes in the oral cavity of a subject comprising the step of applying a composition according to claim 1 to the oral cavity in the form of a toothpaste, mouth rinse, mouth swab, orally dissolving strip or tooth powder.

7. A method of reducing the growth or penetration of decay causing bacteria in a tooth or teeth of a subject by applying the composition according to claim 1 to a tooth or teeth of a subject.

8. A method of treating or reducing periodontal disease in a subject comprising the step of applying to the gingiva of the subject a composition according to claim 1.

9. A method according to claim 8 wherein the periodontal disease is selected from the group consisting of gingivitis and periodontitis.

10. A method according to claim 9 wherein the oral composition is applied to a periodontal pocket of the subject.

11. A method for providing a barrier to microbial activity by applying or incorporating a composition according to claim 1 in the mouth or teeth area of a subject.

12. A composition according to claim 1, wherein the mineralization agent is present in an amount of about 12% to about 20% (w/w) of the composition.

13. A composition according to claim 1, wherein the composition comprises up to about 5% (w/w) of hydrogen peroxide.

* * * * *